(12) United States Patent
Atkins et al.

(10) Patent No.: US 7,393,136 B2
(45) Date of Patent: Jul. 1, 2008

(54) THERMAL PROBE SYSTEMS

(75) Inventors: Anthony George Ernest Atkins, Kent (GB); Graham Poulter, Orpington (GB)

(73) Assignee: Smiths Group plc, London (GB)

( * ) Notice: Subject to any disclaimer, the term of this patent is extended or adjusted under 35 U.S.C. 154(b) by 66 days.

(21) Appl. No.: 11/416,104

(22) Filed: May 3, 2006

(65) Prior Publication Data

US 2006/0289510 A1 Dec. 28, 2006

(30) Foreign Application Priority Data

May 4, 2005 (GB) .................................. 0509043.6

(51) Int. Cl.
*G01K 3/00* (2006.01)
(52) U.S. Cl. ........................ 374/114; 374/141; 374/208
(58) Field of Classification Search ................. 374/141, 374/100, 114, 170, 171, 172, 173, 208
See application file for complete search history.

(56) References Cited

U.S. PATENT DOCUMENTS

| | | | | | |
|---|---|---|---|---|---|
| 2,591,358 | A | * | 4/1952 | Imler | 374/179 |
| 2,728,833 | A | * | 12/1955 | Dickey | 338/28 |
| 2,830,437 | A | * | 4/1958 | Woodward | 60/39.281 |
| 2,877,650 | A | * | 3/1959 | Koletsky | 374/168 |
| 2,884,786 | A | * | 5/1959 | Burk et al. | 374/175 |
| 3,036,464 | A | * | 5/1962 | Beeston, Jr. | 374/166 |
| 3,045,488 | A | * | 7/1962 | Jurs, Jr. et al. | 374/168 |
| 3,061,806 | A | * | 10/1962 | Stevens | 338/28 |
| 3,136,161 | A | * | 6/1964 | Calvert | 374/184 |
| 3,137,170 | A | * | 6/1964 | Astheimer | 250/339.04 |
| 3,161,056 | A | * | 12/1964 | Faus | 73/335.05 |
| 3,164,820 | A | * | 1/1965 | Hulett | 340/581 |
| 3,225,297 | A | * | 12/1965 | Burley et al. | 324/720 |
| 3,363,467 | A | * | 1/1968 | Weir | 324/106 |
| 3,552,645 | A | * | 1/1971 | Boyd | 236/15 R |
| 3,593,577 | A | * | 7/1971 | Monner | 374/34 |
| 3,892,281 | A | * | 7/1975 | Brown | 374/169 |
| 3,926,056 | A | * | 12/1975 | Brown | 73/753 |
| 4,143,549 | A | * | 3/1979 | Koehler | 374/114 |
| 4,528,637 | A | * | 7/1985 | Smith | 702/133 |
| 5,067,820 | A | | 11/1991 | Donohoue et al. | |
| 6,491,425 | B1 | | 12/2002 | Hammiche et al. | |
| 6,608,492 | B1 | * | 8/2003 | Entenmann | 324/706 |

FOREIGN PATENT DOCUMENTS

| | | |
|---|---|---|
| GB | 1079917 | 8/1967 |
| JP | 55125424 | 9/1980 |

OTHER PUBLICATIONS

Hammiche et al., "Mid-infrared Microspectroscopy of Difficult Samples Using Near-Field Photothermal Microspectroscopy", Spectroscopy, vol. 19, No. 2, 2004, pp. 20-42 (missing pages are advertisements).

* cited by examiner

*Primary Examiner*—Gail Verbitsky
(74) *Attorney, Agent, or Firm*—Connolly Bove Lodge & Hutz LLP

(57) ABSTRACT

A thermal probe system has a Wollaston thermal sensor connected in one arm of a bridge. The other arms of the bridge are provided by resistors and a voltage is applied from a low-noise source via several op-amps. The output of the bridge is connected with a primary winding of a step-up transformer, the output of which connects with the input of an output amplifier, which, in turn, provides an output to a display.

7 Claims, 1 Drawing Sheet

THERMAL PROBE SYSTEMS

BACKGROUND OF THE INVENTION

This invention relates to thermal probe systems.

There are several well-known spectroscopy techniques that can be used to make localized infra-red examination of a sample, such as Fourier transform-infrared microspectroscopy and micro-attenuated total reflectance spectroscopy. Recently an alternative technique known as photothermal microspectroscopy has been proposed. This employs a modified form of the probe used in atomic force microscopy to contact and measure the temperature of a localized region on the surface of the sample. The probe employs a small diameter platinum-rhodium wire bent into a V shape with its apex providing the sensing point. As well as sensing the temperature, the probe also acts as a heater to warm the sample where it is contacted. Alternatively, the heating can be achieved by focussing a beam of infrared radiation into a small spot 2 mm in diameter. This can give information about the topography of the sample as well as sub-surface detail resulting from local variations in the thermal conductivity of the sample. Further information about this form of spectroscopy is given in "Mid-infrared Microscopy of Difficult Samples Using Near-Field Photothermal Microspectroscopy" by A Hammiche et al, pps 20-42, Spectroscopy 19(2), February 2004. A problem with this form of spectroscopy is that the noise produced in semiconductor device preamplifiers is high compared with the signal from the probe and makes it very difficult to extract useful information.

It is an object of the present invention to provide an alternative thermal probe system.

According to the present invention there is provided a thermal probe system including a thermal sensing probe and a preamplifier connected with the probe and having an output arranged for connection to an amplifier, the preamplifier including a transformer arranged to increase the signal from the probe.

The system preferably includes a bridge circuit, the probe being connected in an arm of the bridge circuit. The output of the bridge circuit is preferably connected to an input of the transformer. The system may include a voltage source and a plurality of amplifiers connected between the voltage source and resistors of the bridge circuit. The bridge circuit may include adjustable means, such as a potentiometer, for balancing the bridge. The system may include an output amplifier having its input connected with the output of the transformer. The system may include a display arranged to indicate the output of the probe. The probe is preferably a Wollaston thermal sensor. The preamplifier is preferably enclosed within a screened enclosure.

A photothermal system according to the present invention will now be described, by way of example, with reference to the accompanying drawing.

BRIEF DESCRIPTION OF THE DRAWING

The drawing shows the system schematically.

DETAILED DESCRIPTION OF THE PREFERRED EMBODIMENT

Figure 1:
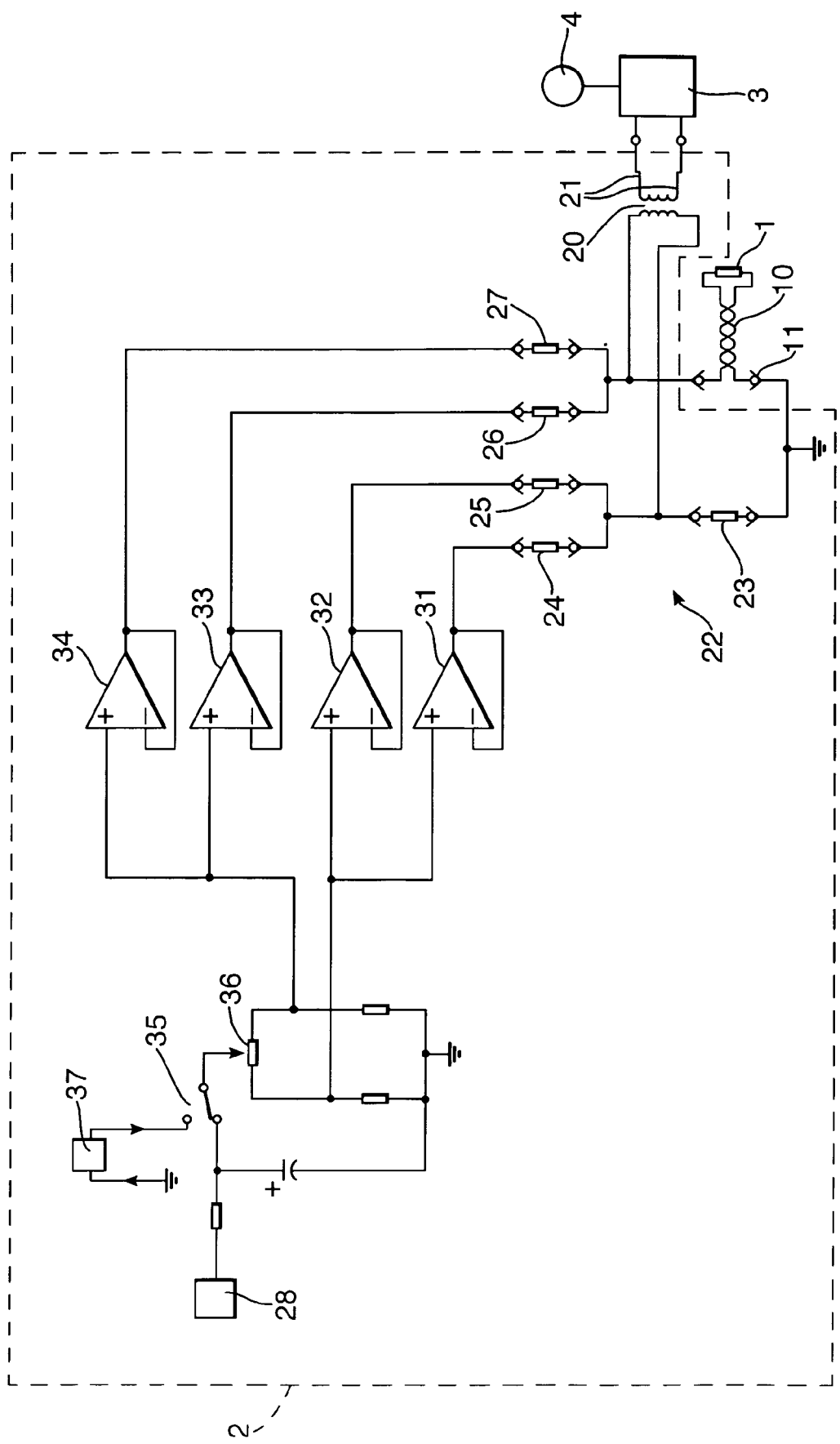

The system includes a photothermal probe or sensor 1 connected with a preamplifier 2, which provides an output to a conventional low-noise output amplifier 3. The amplifier 3 provides an output to a display or other utilisation means 4 indicative of variations in temperature of locations on a sample contacted by the probe.

The probe 1 is a Wollaston thermal sensor including a filament of a 5 µm diameter wire made of platinum with 10% rhodium and formed into a V shape. The free ends of the filament are attached to thicker supporting wires and the apex of the filament provides the sensing tip that is moved over the sample. The sensor 1 requires a bias current between 10-30 mA. The impedance of the sensor 1 can vary from unit to unit but is typically between 2 and 4Ω. The sensor has a 100 mm long twisted pair cable 10 ending in a 2-pin pcb connector 11. Ideally, the lead 10 is kept as short as possible and is tightly twisted to minimize electrical and magnetic pick-up.

The preamplifier 2 provides a dc bias to the probe 1 and amplifies the probe output. The preamplifier includes a low-noise step-up transformer 20 with a winding ratio of 37:1 and is a model JT-34K-DX available from Jensen Transformers, Inc of California. The secondary winding of the transformer 20 provides an output 21 and its primary winding provides an input connected to the output of a Wheatstone bridge circuit 22. The primary winding of the transformer 20 has a low input impedance of around 0.3Ω, which prevents the sensor 1 being connected directly across the transformer.

The Wheatstone bridge 22 has one arm provided by the sensor 1 and connected to ground at one end. A second arm connected to ground is provided by a low-noise wirewound resistor 23. The other end of the resistor 23 is connected to the input of the transformer 20. The other two arms of the bridge 22 are provided by four low-noise wirewound resistors connected as two parallel pairs 24 and 25, and 26 and 27. These two arms have one end connected to the input of the transformer 20. Because of the variation in impedance between different sensors 1, it is preferable that the resistors 23 to 27 are easily replaceable to enable them to be matched to the sensor. The resistors 23 to 27 may be connected by screw-clamp fittings or high quality 2-pin pcb connectors.

A 10 volts dc voltage is applied across the bridge circuit 22 from a commercial low noise voltage source 28, such as an AD588. If this is found to generate unacceptable levels of mains noise, an isolated, re-chargeable battery supply could be used. The source 28 is connected to the bridge circuit 22 via four low-noise op-amps 31 to 34, so as to achieve a total drive current of 60 mA. The amplifiers 31 to 34 could each have a low-pass filter at their input further to minimize noise. The outputs of the op-amps 31 to 34 are connected to respective ones of the resistors 24 to 27. Four amplifiers 31 to 34 are used in order to provide the necessary drive current with a very low noise contribution. It might be possible to use a single amplifier if the current and noise requirements can be met.

The bridge circuit 22 removes the dc bias voltage provided by the source 28 and, if it is perfectly balanced, the system would be insensitive to noise from the bias voltage source. In practice, however, the bridge 22 may not be perfectly balanced and some noise will appear at the input of the transformer 20. The inherent thermal (Johnson) noise from the impedance of the sensor 1 is about $0.2 \, nV/\sqrt{Hz}$ so this appears as a noise level of about $8 \, nV/\sqrt{Hz}$ at the output 21 of the transformer 20. The bridge circuit 22 preferably includes some adjustable means for balancing the bridge such as an adjustable wire-wound potentiometer 36.

As the sensor 1 is exposed to different temperatures, its impedance changes and the output of the bridge circuit 22 also changes, thereby producing an amplified change in the signal at the preamplifier output 21. The amplifier 3 accordingly produces an appropriate output to the display 4.

Instead of applying a dc bias to the sensor 1 it would be possible to use an ac bias by changing a switch 35 in the preamplifier 2 to connect instead to an ac source 37. Typically, the frequency of such a source would be between about 20 kHz and 40 kHz with an amplitude of up to about 5V rms. The signal is preferably buffered in order to drive the fairly low impedance of the Wheatstone bridge 22. The modulated signal from the transformer 20 would then be fed to a lock-in amplifier (not shown) to demodulate it before passing it to the remaining signal processing system. The AC mode would also be used to balance the bridge initially. The AC signal would be applied and the balance of the bridge 22 adjusted to minimize the resulting output signal.

The preamplifier 2 is packaged in a small screened enclosure (indicated by the broken line) to minimize the problem of mains pick-up. The preamplifier enclosure is preferably sited very close to the sensor probe 1 and typically would be located in the sample compartment of another instrument.

The present invention provides an ultra-low-noise preamplifier that enables very small fluctuations in the output of a thermal probe to be amplified and utilized in a useful manner.

The invention claimed is:

1. A thermal probe system comprising: a thermal sensing probe, a preamplifier connected with said probe and an amplifier having an input connected to an output of said preamplifier, wherein said preamplifier comprises: a bridge circuit, said bridge circuit including four arms provided by respective resistors, one of which is provided by said probe; a voltage source; a plurality of amplifiers connected between said voltage source and others of said resistors; and a transformer having an input connected to an output of said bridge circuit so as to increase the signal from the bridge circuit to thereby increase the signal from said probe at the output of said preamplifier.

2. A thermal probe system according to claim 1, wherein said preamplifier is enclosed within a screened enclosure.

3. A thermal probe system according to claim 1, wherein said probe is a Wollaston thermal sensor.

4. A thermal probe system according to claim 1, wherein the system includes a display, and wherein said display is arranged to indicate the output of said probe.

5. A thermal probe system according to claim 1, wherein said bridge circuit includes an adjustable device for balancing said bridge circuit.

6. A thermal probe system according to claim 5, wherein said adjustable device is a potentiometer.

7. A thermal probe system comprising: a thermal sensing probe and a preamplifier connected with the probe, wherein said preamplifier includes a voltage source connected with inputs of a plurality of op-amps, wherein outputs of said op-amps are connected with resistors forming two arms of a bridge circuit, wherein another arm of said bridge circuit is provided by said thermal sensing probe and a further arm is provided by a low-noise resistor, wherein a primary winding of a step-up transformer is connected across an output of the bridge circuit and a secondary winding of the transformer is connected with an input of a low-noise amplifier arranged to provide an output indication of said probe.

* * * * *